(12) United States Patent
Dhar-Mascareno et al.

(10) Patent No.: US 9,789,159 B2
(45) Date of Patent: Oct. 17, 2017

(54) DIAGNOSIS AND TREATMENT OF PROSTATE CANCER

(75) Inventors: Manya Dhar-Mascareno, East Northport, NY (US); Eduardo J. Mascareno, East Northport, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/006,406

(22) PCT Filed: Mar. 22, 2012

(86) PCT No.: PCT/US2012/030105
§ 371 (c)(1),
(2), (4) Date: Apr. 28, 2014

(87) PCT Pub. No.: WO2012/129395
PCT Pub. Date: Sep. 27, 2012

(65) Prior Publication Data
US 2014/0227172 A1    Aug. 14, 2014

Related U.S. Application Data

(60) Provisional application No. 61/466,517, filed on Mar. 23, 2011.

(51) Int. Cl.
| | |
|---|---|
| *C07K 16/00* | (2006.01) |
| *A61K 38/17* | (2006.01) |
| *G01N 33/574* | (2006.01) |
| *A61K 31/353* | (2006.01) |
| *A61K 45/06* | (2006.01) |
| *A61K 51/00* | (2006.01) |
| *C07K 16/18* | (2006.01) |

(52) U.S. Cl.
CPC ........ *A61K 38/1709* (2013.01); *A61K 31/353* (2013.01); *A61K 45/06* (2013.01); *A61K 51/00* (2013.01); *C07K 16/18* (2013.01); *G01N 33/57434* (2013.01)

(58) Field of Classification Search
None
See application file for complete search history.

(56) References Cited

PUBLICATIONS

Gurumurthy et al (J Mol Biol, 2008, 378(2): 302-317).*
Berkofsky—Fessler et al (Mol Cancer Ther, 2009, 8(9): 2518-2525).*
Stone et al (Int J Cancer, 2003, 104: 73-84).*
Ouchida et al (Genes to Cells, 2003, 8: 95-107).*
Dressman et al (Clin Cancer Res, 2006, 12(3 Pt 1): 819-826).*
Du et al (Anal Chem, 2011, 83(17): 6580-6585).*
Berkofsky-Fessler W. et al., "Preclinical Biomarkers for a Cyclin-Dependent Kinase Inhibitor Translate to Candidate Pharmacodynamic Biomarkers in Phase I Patients", Mol Cancer Ther 8:2517-2525 (Sep. 2009).
Ouch Ida R. et al., "Suppression of NF-KB-Dependent Gene Expression by a Hexamethylene Bisacetamide-Inducible Protein HEXIM1 in Human Vascular Smooth Muscle Cells", Genes to Cells 8:95-107 (2003).

* cited by examiner

*Primary Examiner* — Sean Aeder
(74) *Attorney, Agent, or Firm* — Scully, Scott, Murphy & Presser, P.C.

(57) ABSTRACT

The methods of the present disclosure are directed toward methods of diagnosis and treatment of cancer in a subject. The present disclosure provides methods of diagnosing abnormal cells in a subject by measuring the level of Hexim-1 in a sample from the subject, where elevated levels of Hexim-1 indicate abnormal cells. This disclosure further provides methods of treating cancer or hyperplasia, comprising administering to a subject in need thereof a therapeutically effective amount of Hexim-1 or an activator of Hexim-1 expression or activity.

5 Claims, 10 Drawing Sheets

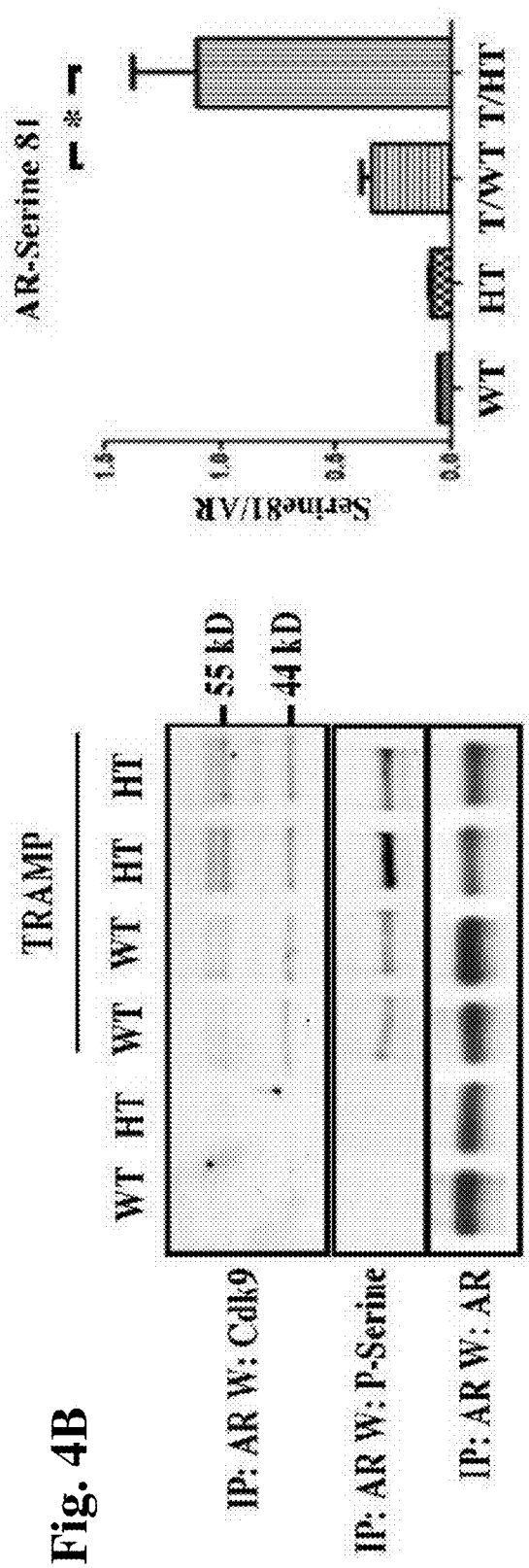

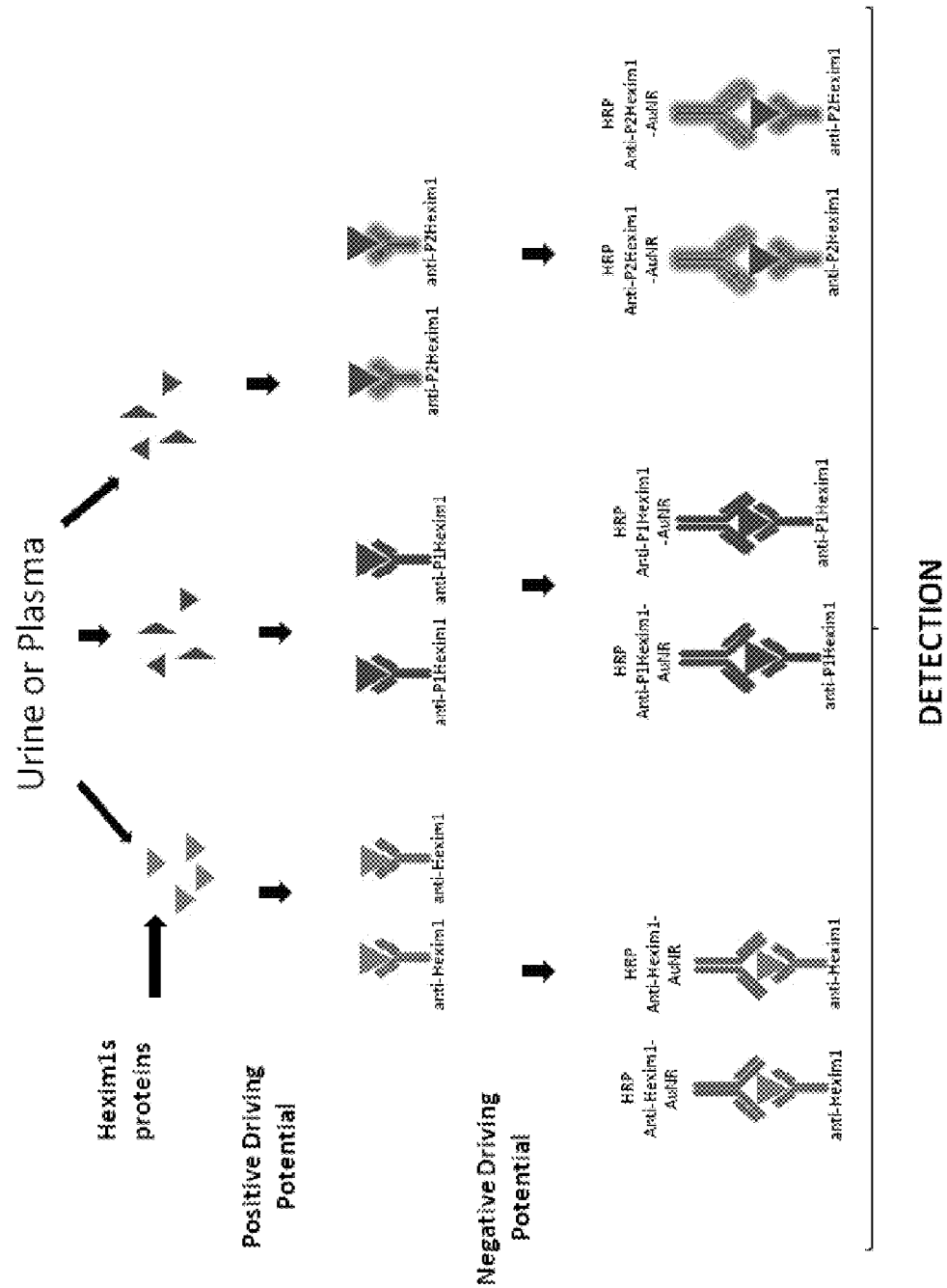

DIAGNOSIS AND TREATMENT OF PROSTATE CANCER

CROSS-REFERENCE TO RELATED APPLICATIONS

This application claims the benefit of U.S. provisional application 61/466,517, filed Mar. 23, 2011, which is incorporated herein in its entirety.

INCORPORATION BY REFERENCE OF SEQUENCE LISTING

The Sequence Listing in the ASCII text file, named as 27274_SequenceListing.txt of 2 KB, created on Sep. 30, 2014, and submitted to the United States Patent and Trademark Office via EFS-Web, is incorporated herein by reference.

BACKGROUND OF THE DISCLOSURE

The National Cancer Institute estimates that about ten million Americans have or have had some form of cancer. Overall costs of the disease are $126 billion annually. According to the American Cancer Institute, prostate cancer is the second leading cause of cancer death in men in the United States.

Data from the National Institute of Cancer indicates that the current Prostate-specific antigen (PSA) test can fail to detect prostate cancer in some patients and lead to unnecessary biopsies for many others. Only 25-30% of men who have a biopsy due to elevated PSA levels actually have prostate cancer.

A more accurate test is desired to substantiate the diagnosis of prostatic adenocarcinoma and exclude mimicking conditions including atrophy, atypical adenomatous hyperplasia (AAH), nephrogenic adenoma and mesonephric hyperplasia. Current immunohistochemical diagnosis of prostate cancer depends on markers because no absolutely specific and sensitive marker for prostate cancer has been discovered. Even after current immunohistochemical diagnosis, the diagnosis of minimal prostatic adenocarcinoma can be ambiguous in prostate needle biopsy tissues.

Hexim-1 is a regulatory component of the positive elongation pTEFb complex and interacts with Cyclin T1, the partner of cyclin dependent kinase 9 (Cdk9), a serine kinase. The structure and further description of Hexim-1 is described by Dames et al. (2007), *Proc. Natl. Acad. Sci USA* 104:14312-7. Gene transcription by RNA polymerase II (RNA Pol II) proceeds by the steps of (a) initiation of RNA transcription, (b) elongation of the RNA transcript, and (c) termination of the RNA transcript. Each stage is highly regulated and requires the participation of multiple factors. When Hexim-1 is complexed within the pTEFb complex, the Cdk9 serine kinase is inactive. However, when Hexim-1 is released from the pTEFb complex, Cdk9 within the pTEFb complex can phosphorylate the serine residues of the carboxyl terminus domain (CTD) of RNA Pol II within the consensus site Tyr-Ser-Pro-Thr-Ser-Pro-Ser (SEQ ID NO: 6). Following phosphorylation of the CTD, RNA Pol II enters into the elongation phase. Thus, in the presence of Hexim-1 in the pTEFb complex, transcription does not proceed, while in the absence of Hexim-1, Cdk9 phosphorylates the CTD of RNA Pol II and transcription elongation occurs.

SUMMARY OF THE INVENTION

The present disclosure provides methods of detecting abnormal cells in a subject by measuring the level of Hexim-1 in a cell sample obtained from the subject, where elevated levels of Hexim-1 identifies cells as abnormal. Abnormal cells may be hyperplastic or cancerous.

The present disclosure also provides methods of diagnosing cancer or hyperplasia in a subject, by measuring Hexim-1 levels in the nucleus and cytoplasm of a cell sample obtained from the subject. Hyperplasia is identified by elevated levels of Hexim-1 in the nucleus but not the cytoplasm, while cancer is identified by elevated levels of Hexim-1 in at least the cytoplasm.

This disclosure further provides methods of monitoring a hyperplastic or cancerous condition in a subject by measuring the level of Hexim-1 in a sample from the subject. Here, elevated levels of Hexim-1 identify worsening of the hyperplastic or cancerous condition, while reduced levels of Hexim-1 identify improvement of the hyperplastic or cancerous condition.

In addition, this disclosure provides methods to determine the effectiveness of a cancer therapy in a subject, where elevated levels of Hexim-1 identify the cancer therapy as ineffective, and wherein reduced levels of Hexim-1 identify said cancer therapy as effective.

This disclosure also provides kits for detecting the presence of abnormal cells in a sample, the kit including one or more agents to detect Hexim-1. The kit can include one or more agents to detect phosphorylated Hexim-1. The kit can also include an electrochemical immunosensor. The kit can further include instructions for use in detecting abnormal cells.

This disclosure further provides methods of treating cancer or hyperplasia, comprising administering to a subject in need thereof a therapeutically effective amount of Hexim-1 or an activator of Hexim-1 expression or activity or an inhibitor of Hexim-1 phosphorylation. This treatment can be combined with one or more additional cancer treatments.

Figure 4A:
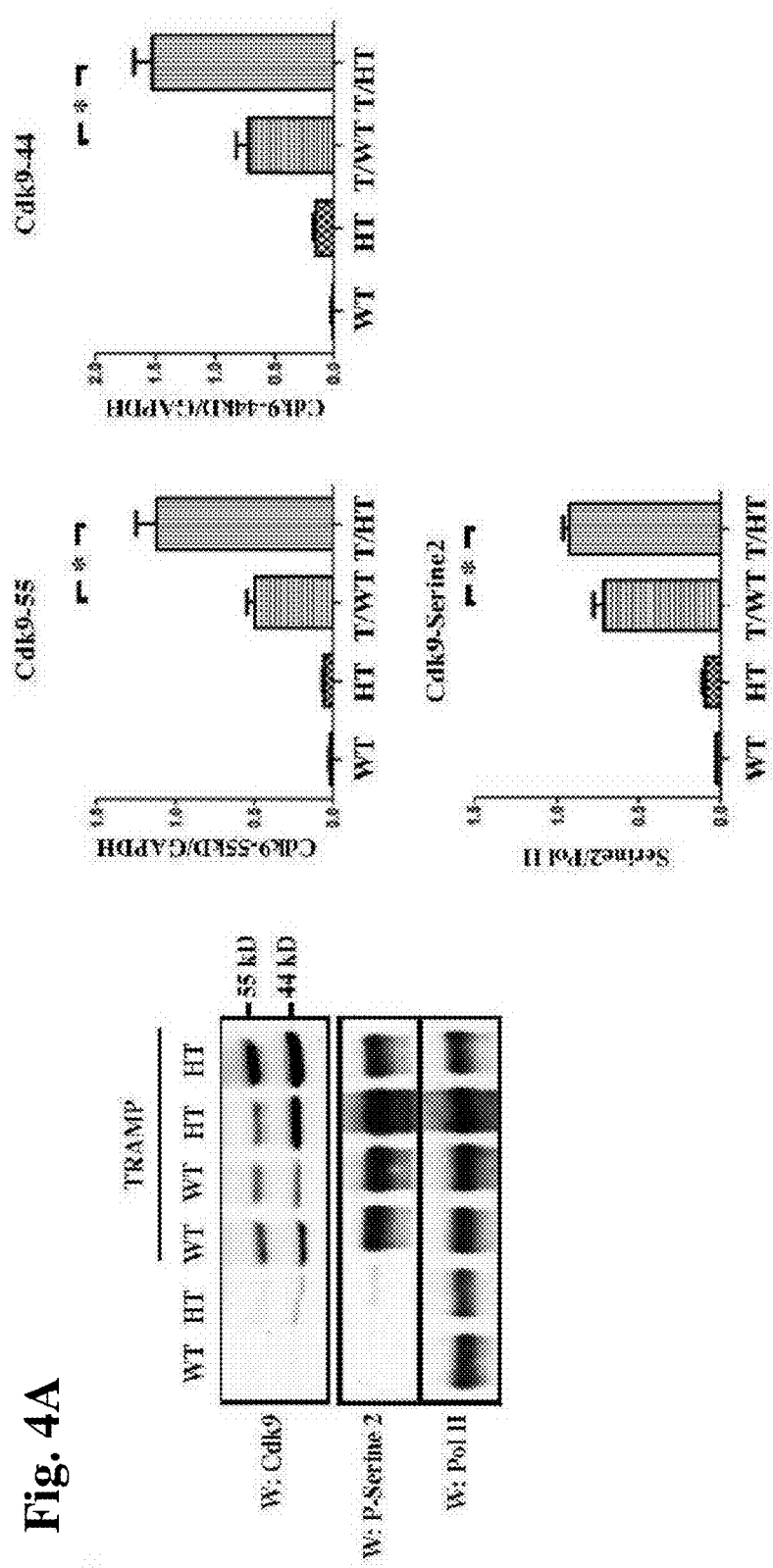
Figure 4C:
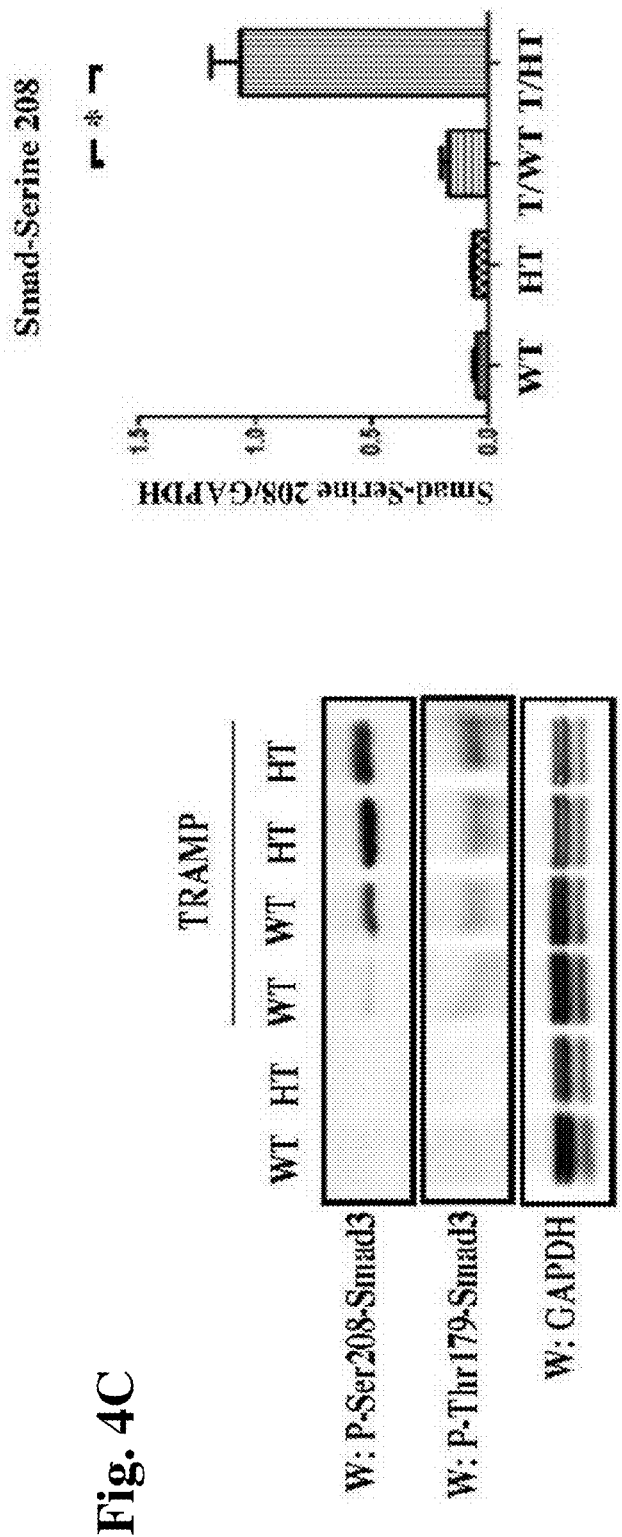

FIG. 4: Hexim-1 as a regulator of Cdk9 activity. A: Total prostate protein extracts from TRAMP and TRAMP; Hexim-1+/− mice were used to evaluate Cdk9 expression and Cdk9-dependent serine-2 phosphorylation activity. Total RNA Pol II expression was used as loading control. Representative Western blot with duplicate samples from the transgenic mice are shown. Data are expressed as mean+/−SE of three independent experiments in triplicate. Cdk9-55 kDa and Cdk9-44 kDa expressions, *P<0.0001 TRAMP; Hexim-1+/− versus TRAMP. Cdk9-dependent phosphoserine 2 activity, *P<0.0001 TRAMP; Hexim-1+/− versus TRAMP. B: The role of Cdk9 activity as a serine kinase protein on the androgen receptor was evaluated by immunoprecipitation. Upper panel shows interaction between Cdk9 and the androgen receptor in extracts from both TRAMP-WT and TRAMP-HT. Middle panel revealed increased serine-81 phosphorylation of the androgen receptor in the bigenic mice (TRAMP-HT). Data are expressed as mean+/−SE of three independent experiments in duplicate. Serine 81 phosphorylation, *P<0.0027 TRAMP/Hexim-1+/− versus TRAMP. Lower panel represents the loading control as evaluated by the expression levels of total androgen receptor. WT=C57BL6. HT=C57BL6; Hexim-1+/−. TRAMP-WT=C57BL/6; TRAMP. TRAMP-HT=C57BL/6; TRAMP; Hexim-1+/−. C: Western blot showing the levels of Cdk9-dependent serine-208 phosphorylation of Smad3 (upper panel), and phosphothreonine-179 phosphorylation (middle panel) in extract from prostate tissues. GAPDH was used as a loading control. Data are expressed as mean+/−SE of four independent experiments. Serine 208 phosphorylation, *P<0.0001 TRAMP/Hexim-1+/− versus TRAMP.

Figure 5A:
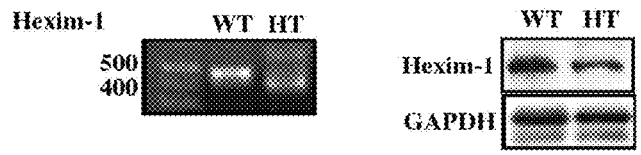

FIG. 5: Hexim-1 regulates TGF-β/SMAD transcriptional activity. A: Genomic DNA was obtained from TRAMP-C2 cell line (WT) and the TRAMP-C2-Hexim-1+/− cell line (HT) to perform a PCR reaction to identify the wild type and the derived Hexim-1 heterozygosity, respectively. Right panel shows decreased Hexim-1 protein expression in the TRAMP-C2-Hexim-1+/− (HT) cell line. GAPDH was used as loading control. B: Transient transfection experiment of the reporter plasmid pSM22 luciferase in TRAMP-C2 and TRAMP-C2-Hexim-1+/− cell line expression subjected to different time point of TGF-β (5 ng/ml) treatment. Data are expressed as mean+/−SEM of four independent experiments. *P<0.05 TRAMP-C2 versus TRAMP-C2-CLP-1+/− treated with TGF-β. C: Increased TGF-β mediated transcriptional activity requires an intact serine/threonine linker residue in Smad3. A co-transfection experiment as before was performed in presence of a wild-type Smad3 expression vector (pSmad3) or a mutant Smad3 carrying a substitution mutation of the linker region (pMLSmad3) followed by TGF-β treatment (5 ng/ml) at different time points. Data are expressed as mean+/−SEM of four independent experiments. *P<0.05 TRAMP-C2-CLP-1+/− versus TRAMP-C2-CLP1+/−+pSmad3.

FIG. 6: Hexim-1 heterozygosity in TRAMP accelerates prostate cancer. A: Hematoxylin-Eosin staining of anterior prostate of WT, HT, TRAMP-WT, and TRAMP-HT mice at 24 and 36 weeks of age. High-grade prostatic intraepithelial neoplasia (High PIN), carcinoma in situ (CIS) with extensive pleomorphism and cribiform structures and invasive carcinoma in TRAMP Hexim-1+/− mice was observed at an earlier time frame than in the TRAMP background. The images were obtained at 20× magnification. B: Expression of Hexim-1 was evaluated by immunofluorescence in C57BL/6-TRAMP and C57BL/6^TRAMP Hexim-1+/− sections. WT-TRAMP revealed the nuclear staining of Hexim-1 protein as confirmed by DAPI. However, Hexim-1-HT-TRAMP shows uniform distribution of Hexim-1 protein in the nuclei and cytoplasm. DAPI staining identifies the nuclear localization of the High PIN epithelium. The images were obtained at 40× magnification using a Nikon Microphot-SA microscope and SPOT Software version 4.6.

Figure 7:
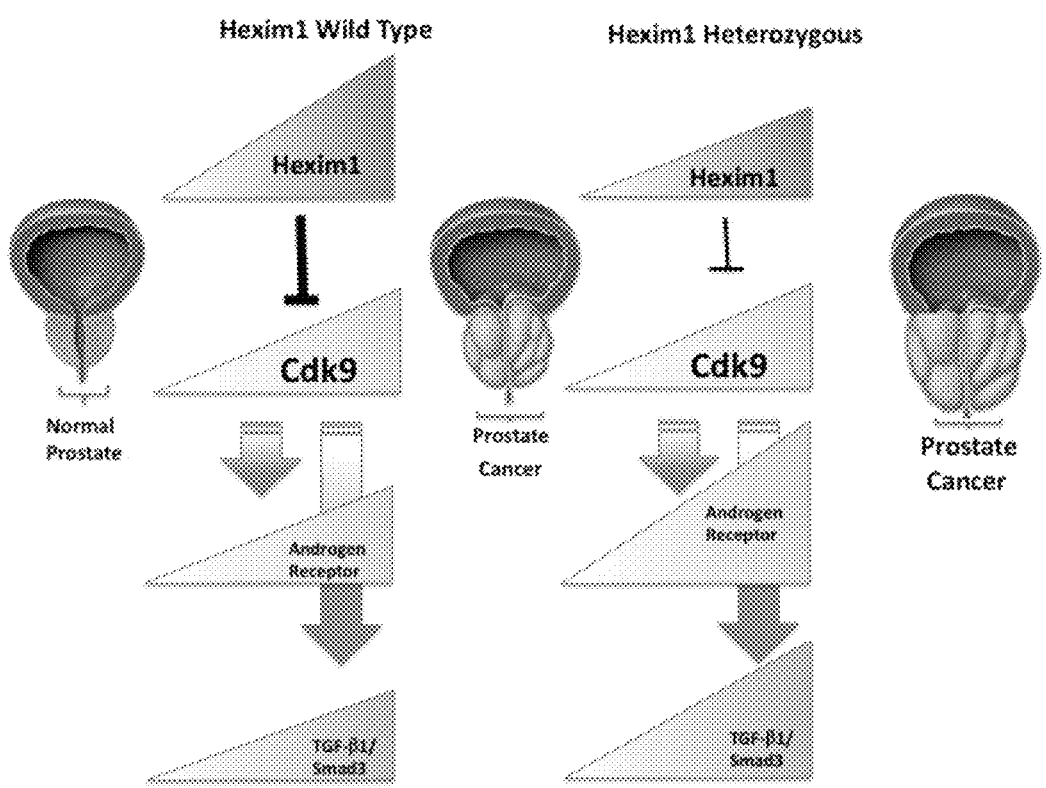

FIG. 7. Model for the role of Hexim-1 in prostate cancer development.

FIG. 8. Electrochemical Immunosensor Assay (EIA) or "Barcode" technology for detection of Hexim-1 in a sample.

DETAILED DESCRIPTION OF THE INVENTION

The present disclosure provides improved methods and kits for diagnosis and monitoring of cancers, based on measuring levels of hexamethylene bisacetamide inducible protein 1 (Hexim-1). The improvements provide an increased accuracy of diagnosis and monitoring of cancerous and pre-cancerous conditions.

The inventors have discovered that Hexim-1, a protein that mediates transcription in the nucleus, is dramatically up-regulated in cancer and hyperplastic conditions. In addition to up-regulation of Hexim-1 expression, Hexim-1 localization within the cell changes during the course of cancer progression. Thus, measurements of Hexim-1 expression and/or localization can be used to diagnose and monitor disease states, monitor the efficacy of therapeutic regimens, and provide post-treatment surveillance.

The present disclosure provides methods of detecting abnormal cells in a subject by measuring the level of Hexim-1 in a sample from the subject, where elevated levels of Hexim-1 indicate the presence of abnormal cells. Abnormal cells may be hyperplastic or cancerous.

Initially a sample of cells is taken from the subject. The sample may be a sample of sputum, cerebrospinal fluid, blood, blood fractions such as serum and plasma, blood cells, tissue or fine needle biopsy samples, urine, peritoneal fluid, and pleural fluid, or cells there from. In one example, the sample is a blood sample. In another example, the sample is a urine sample obtained following digital stimulation of the prostate (typically, three sweeps on either side of the prostate by rectal digital insertion).

In addition to increases in Hexim-1 expression during cancer progression, posttranslational modification via phosphorylation of Hexim-1, which is absent in benign hyperplasia, is seen in the progression to cancer. Therefore, methods to identify the presence of phosphorylated Hexim-1, such as phospho-specific anti Hexim-1 antibodies, can also be used to distinguish between normal growth (benign hyperplasia) and abnormal deregulated growth such as adenocarcinomas and metastasis.

Hexim-1 levels can be measured from a patient sample using any suitable technique, including immunohistochemical techniques, gel electrophoresis, Northern, Western, or Southern blots, polymerase chain reaction (PCR) and PCR techniques such as Real Time PCR, quantitative Real Time PCR, reverse-transcriptase PCR, and suitable assays including ELISA, nanoparticle based assays, biochip based assays, magnetic immunoassays, radioimmunoassay, lateral flow test, Surround Optical Fiber Immunoassay (SOFIA), and assays incorporating horseradish peroxidase. In one example, Hexim-1 is measured by histopathological examination of tissue sections utilizing a Hexim-1-specific marker, such as a Hexim-1 antibody.

In another example, Hexim-1 is measured by a modified electrochemical immunosensor assay (EIA), a platform technology that enables measurement of multiple analytes in a sample (Du, et al., *Anal. Chem.* 83:6580-6585 (2011)). EIA can discriminate between analytes either by modifying the spatial resolution between analytes, or by using multiple labels. Multiple labels may be enzymes, metal ions and/or nanoparticles. To discriminate by modifying spatial resolution, EIA may incorporate a single-enzyme label, which provides simplicity but requires separation between analytes/nanocomponents to avoid signal interference between adjacent electrodes.

In one example utilizing EIA technology, detection is achieved by incorporating nanomaterial into the assay which enhances signal amplification. For example, enzyme functionalized nanoparticles, used to enhance sensitivity of detection, direct large quantities of detecting enzyme (for example, horseradish peroxidase/HRP), towards an individual immunological detection reaction. Nanomaterials for use in EIA include carbon nanotubes, carbon nanospheres, grapheme oxide, gold nanoparticles, silica nanoparticles, and carboxylated magnetic beads. Additionally, immunoreactions on an immunosensor can be accelerated by magnetic stirring, low-power microwave, electric field and/or electrophoresis-assisted immunoassay.

In another example of EIA technology, simultaneous detection of Hexim-1 and one or both of the phosphorylated Hexim-1 proteins P1-Hexim-1 and P2-Hexim-1 is achieved through a multiplexed EIA that combines an enzyme-label amplification approach with an electric field driven acceleration method.

In this example using HRP as a detecting enzyme and gold nanorods (AuNR) as a carrier to co-immobilize HRP, an EIA assay is illustrated for detection of antibodies that specifically recognize either Hexim-1, or P1-Hexim-1 or P2-Hexim-1 (FIG. 8). In this example the following complexes can be obtained: HRP/anti-Hexim-1-AuNR, HRP/anti-P1-Hexim-1-AuNR, and/or HRP/anti-P2-Hexim-1-AuNR. A positive driving potential can be applied to accelerate the transport of negatively charged Hexim-1 proteins (Hexim-1, P1-Hexim-1, and P2-Hexim-1) to the electrode surface, followed by a low negative driving potential that accelerates the transport of positively charged HRP/anti-Hexim-1-AuNR, HRP/anti-P1-Hexim-1-AuNR, and HRP/anti-P2-Hexim-1-AuNR bioconjugates forming the following specific immuno-sandwich: anti-Hexim-1/Hexim-1 protein/HRP/anti-Hexim-1-AuNR, or anti-P1-Hexim-1/P1Hexim-1 protein/HRP/P1-anti-Hexim-1-AuNR, or anti-P2-Hexim-1/P2Hexim-1 protein/HRP/anti P2-Hexim-1-AuNR in each working electrode. Measurement of activity at each electrode by voltammetry indicates the presence and amount of Hexim-1, P1-Hexim-1, and P2-Hexim-1 in a sample.

The absence of detectable levels of any of Hexim-1, P1-Hexim-1, or P2-Hexim-1 indicates that the subject has normal tissues, while the presence of detectable levels of Hexim-1, where detectable levels are indicated by measurement of current at, for example, 0.2 to 1 µA at a specific redox peak, such as approximately −0.256 V and approximately −0.238 V, indicates tissue abnormality, such as prostate, breast, colon, pancreatic, lung, gastric, or bladder hyperplasia. Further, elevated levels of Hexim-1, in addition to levels of P1-Hexim-1 and/or P2-Hexim-1, where elevated levels are indicated by measurement of current at or above 1 µA at a specific redox peak, such as approximately −0.256 V and approximately −0.238 V, indicates cancer.

Hexim-1 levels may be elevated, or increased, by 10%, 20%, 30%, 40%, 50%, 60%, 70%, 80%, 90%, or 100% or more. Hexim-1 levels may also be elevated, or increased, by two-fold (i.e., a doubling of Hexim-1 levels), three-fold (i.e., a tripling of Hexim-1 levels), four-fold (i.e., an increase by four times the level of Hexim-1), or five-fold or greater. Hexim-1 levels may be phosphorylated or unphosphorylated Hexim-1 levels. In one example, abnormal cells are indicated if a subject has Hexim-1 levels that are 10%, 20%, 30%, 40%, or 50% or greater than the Hexim-1 levels in a control. Similarly, Hexim-1 levels can decrease, for example in response to treatment. Thus, Hexim-1 levels can decrease by 10%, 20%, 30%, 40%, 50%, 60%, 70%, 80%, 90%, or 100% or more. An increase in the level of Hexim-1 can be determined from one measure in a subject of interest relative to control (e.g., a value or a range of values for normal, i.e., healthy, individuals). Alternatively, Hexim-1 levels can be compared to the levels of Hexim-1 in another sample from the same subject at an earlier or later time point.

Once the level of Hexim-1 is measured in the sample, the measured levels can be used to diagnose the cells as normal or abnormal. If the measured level of Hexim-1 is below, equal to, or less than 10% above the level in a control, the cells of the subject are diagnosed as normal. If the measured level of Hexim-1 is 10% or greater than control levels, the cells of the subject are diagnosed as abnormal, i.e., hyperplastic or tumorigenic. The level of Hexim-1 in a control can depend on the tissue type being examined. The level of Hexim-1 in a control can also depend on the sensitivity of the method used to measure Hexim-1 levels. In many assays, levels of Hexim-1 can range from undetectable to detectable. For example, using some common immunoassay-based tools, such as immunohistochemistry or ELISA, and also by PCR, levels of Hexim-1 can be undetectable in normal cell and/or tissue samples. Thus, where Hexim-1 levels are undetectable in controls, any detectable level of Hexim-1 is considered elevated and abnormal. This is true for any method of measurement where the level of Hexim-1 is not detectable in a control.

Hexim-1 is usually found in most normal somatic cells at extremely low levels. For example, the mRNA encoding Hexim-1 protein is extremely rare or absent in normal cells. It will thus be apparent that, when highly sensitive assays for Hexim-1 is desired, it will sometimes be advantageous to incorporate signal or target amplification technologies into the assay format. See, for example, Plenat et al., 1997, Ann. Pathol. 17:17 (fluoresceinyl-tyramide signal amplification); Zehbe et al., 1997, J. Pathol. 150:1553 (catalyzed reporter deposition); other references listed herein (e.g., for bDNA signal amplification, for PCR and other target amplification formats); and other techniques known in the art.

It is often unnecessary to quantitate the Hexim-1 mRNA or protein in the assays disclosed herein, because the detection of Hexim-1 (under assay conditions in which the product is not detectable in control) is in itself sufficient for a diagnosis. As another example, when the levels of product found in a test (e.g., tumor) and control (e.g., healthy cell) samples are directly compared, quantitation may be superfluous.

When desired, however, levels of Hexim-1 measured in the assays described herein may be described in a variety of ways, depending on the method of measurement and convenience. Thus, normal, diagnostic, prognostic, high or low levels of Hexim-1 may be expressed as standard units of weight per quantity of biological sample (e.g., picograms per gram tissue, picograms per $10^{12}$ cells), as a number of molecules per quantity of biological sample (e.g., transcripts/cell, moles/cell), as units of activity per cell or per other unit quantity, or by similar methods. The levels of Hexim-1 can also be expressed in relation to the quantity of another molecule; examples include: levels of Hexim-1 transcripts in sample/levels of 28S rRNA transcripts in sample; nanograms of Hexim-1 protein/nanograms of total protein; and the like.

When measuring levels of Hexim-1 in two (or more) different samples, it will sometimes be useful to have a common basis of comparison for the two samples. For example, when comparing a sample of normal tissue and a sample of cancerous tissue, equal amounts of tissue (by weight, volume, number of cells, etc.) can be compared. Alternatively, equivalents of a marker molecule (e.g., 28S rRNA, actin) may be used. For example, the levels of Hexim-1 in a healthy tissue sample containing 10 picograms of 28S rRNA can be compared to a sample of diseased tissue containing the same amount of 28S rRNA.

It will also be recognized by those of skill that virtually any of the assays described herein can be designed to be quantitative. Typically, a known quantity or source of Hexim-1 is used to calibrate the assay.

In certain embodiments, assay formats are chosen that detect the presence, absence, or abundance of Hexim-1 in each cell in a sample (or in a representative sampling). Examples of such formats include those that detect a signal by histology (e.g., immunohistochemistry with signal-enhancing or target-enhancing amplification steps) or fluorescence-activated cell analysis or cell sorting (FACS). These formats are particularly advantageous when dealing with a highly heterogeneous cell population (e.g., containing multiple cells types in which only one or a few types have elevated Hexim-1 levels, or a population of similar cells expressing Hexim-1 at different levels).

In an EIA assay, detectable levels can be indicated by measurement of square wave voltammetry (SWV) at a current, for example, at or above 0.1, 0.2, 0.3, 0.4, 0.5, 0.6, 0.7, 0.8, 0.9, or 1.0 µA at a specific redox peak between −0.200 to −0.300 V, or between −0.220 and −0.280 V, or between −0.230 and −0.266 V, such as approximately −0.256 V and/or approximately −0.238 V. Further, elevated levels of Hexim-1, as measured by SWV in an EIA, are indicated by measurement of current at or above 1.0, 1.1, 1.2, 1.3, 1.4, 1.5, 2.0, 2.2, 2.5, 2.8, 3.0, 3.5, 4.0, 4.5, 5.0, 5.5, 6.0, 6.5, 7.0, 7.5, 8.0, 8.5, or 9.0 µA, at a specific redox peak between −0.200 to −0.300 V, or between −0.220 and −0.280 V, or between −0.230 and −0.266 V, such as approximately −0.256 V and approximately −0.238 V.

This disclosure further provides kits for detecting the level of Hexim-1 in a sample. The kit includes one or more reagents to detect Hexim-1 or to quantify expression of the Hexim-1 gene, including, for example, nucleic acid primers and probes that specifically bind to the Hexim-1 gene, RNA, cDNA, or portions thereof, along with proteins, peptides, antibodies, and control primers, probes, oligonucleotides, proteins, peptides and antibodies. The kit can further include other suitable reagents including enzymes (e.g., reverse transcriptases, DNA polymerases, ligases), buffers, reagents (labels, dNTPs) for assisting in Hexim-1 detection. The kit may also include one or more tissue-specific controls against which Hexim-1 detection is measured, for determination of normal or elevated/abnormal Hexim-1 levels.

The kits may include alternatively, or in combination with any of the other components described herein, an antibody that specifically binds to Hexim-1 polypeptides or subsequences thereof. The antibody can be monoclonal or polyclonal. The antibody can be conjugated to another moiety such as a label and/or it can be immobilized on a solid support (substrate). The kit(s) may also contain a second antibody for detection of Hexim-1 polypeptide/antibody complexes or for detection of hybridized nucleic acid probes, as well as one or more Hexim-1 peptides or proteins for use as control or other reagents.

The antibody or hybridization probe may be free or immobilized on a solid support such as a test tube, a microtiter plate, a dipstick and the like. The kit may also contain instructional materials teaching the use of the antibody or hybridization probe in an assay for the detection of Hexim-1. The kit may contain appropriate reagents for detection of labels, or for labelling positive and negative controls, washing solutions, dilution buffers and the like.

In an example, a kit for measuring Hexim-1 includes primary antibodies specific for Hexim-1 and/or primary antibodies specific for one or more forms of phosphorylated Hexim-1. The kit can optionally include a means or agent to detect the primary antibodies, such as one or more enzymes, metal ions and/or nanomaterials. The kit can further optionally include one or more electrode-based immunosensing means, such as an electrochemical immunosensor or microplate. The immunosensor can be a multiplex immunosensor for use in a sandwich immunoassay. The kit can additionally include a means or reagent to enhance sensitivity of detection, such as nanomaterials or secondary antibodies that recognize the primary antibodies. The kit can in addition include one or more means to accelerate the reaction. The kit can further include instructions on how to measure levels of Hexim-1 using the kit materials.

The terms "tumorigenic" and "cancerous" are used interchangeably herein to describe cells or tissues exhibiting uncontrolled proliferation and potential to invade surrounding tissues. A "cancerous condition" or "cancer" refers to a condition characterized by tumorigenic or cancerous cells.

The term "hyperplastic" is meant to describe cells or tissues that are undergoing above normal proliferation but are not cancerous. Accordingly, "hyperplasia" or a "hyperplastic condition" refers to a condition, typically a precancerous condition, characterized by abnormal cell proliferation. Hyperplasia can be a precursor to any cancer type disclosed herein.

The term "abnormal" is meant to describe cells or tissues that are either tumorigenic or hyperplastic.

"Normal" cells or tissues are cells or tissues that are not undergoing hyperplasia and are not tumorigenic. "Normal" levels of Hexim-1 indicate levels of Hexim-1 found in normal cells or tissues.

In one example, Hexim-1 levels in a sample of prostate cells from a subject are measured. If Hexim-1 levels are below, equal to, or less than 10% higher than the levels in a control representing normal prostate cells, the subject prostate cells are diagnosed as normal. For example, if Hexim-1 levels are undetectable in the control and in the subject sample are both undetectable, the subject prostate cells are diagnosed as normal. In contrast, if Hexim-1 levels are 10% or greater compared to control levels, for example where control Hexim-1 levels are undetectable but Hexim-1 levels in the subject prostate cells are detected, the subject prostate cells are diagnosed as abnormal, and prostate cancer or hyperplasia is diagnosed.

The present disclosure also provides methods of diagnosing cancer or hyperplasia in a subject, by measuring Hexim-1 levels in the nucleus and cytoplasm of a sample of cells from the subject. By "diagnosing" is meant determining whether a subject likely has a condition of concern. The condition of concern may be, for example, cancer, hyperplasia, or abnormal cells. Hyperplasia is indicated if elevated levels of Hexim-1 are found in the nucleus but not the cytoplasm, while cancer is indicated if elevated levels of Hexim-1 are found in the cytoplasm.

The inventors have discovered that Hexim-1 is not detectable in normal cells using standard immunological techniques; however, nuclear localization of Hexim-1 is present in benign, hyperplastic cells. Further, Hexim-1 in adenocarcinomic or tumorigenic cells is found in the nucleus as well as the cytoplasm of the prostate cells; thus, the presence of Hexim-1 in the cytoplasm is evidence of cancer.

Levels of Hexim-1 may be separately measured in the nucleus and the cytoplasm of the cells by various techniques, including immunohistochemistry of tissue sections, or by separation of nuclear and cytoplasmic contents prior to measurement, such as by partial cell lysis and centrifugation to separate cell components followed by measurement of Hexim-1 in nuclear and cytoplasmic fractions. Once the level of Hexim-1 is measured in the nucleus and the cytoplasm, the measured levels can be used to diagnose hyperplasia or cancer. If the measured level of Hexim-1 in cytoplasm and nucleus is comparable to control levels, i.e., low or undetectable, the cells are indicated as normal. If the measured level of Hexim-1 is higher than control levels in the nucleus alone, the cells are indicated as hyperplastic but not tumorigenic. If the measured level of Hexim-1 is higher than control levels in the nucleus and cytoplasm, the cells are indicated as tumorigenic.

The term "detectable" is meant to describe the amount of Hexim-1, above which any level of expression can be determined using a suitable method including, but not limited to, enzyme linked immunosorbent assay (ELISA), immunohistochemistry and polymerase chain reaction (PCR). Compared to controls where Hexim-1 levels are undetectable, detectable levels are also considered elevated levels.

In addition, methods to identify phosphorylated Hexim-1, such as phospho-specific anti-Hexim-1 antibodies, can be used to distinguish between benign hyperplasia, which is characterized by the presence of Hexim-1 but not phosphorylated Hexim-1, and cancer, which is characterized by the presence of phosphorylated Hexim-1, alone or in addition to unphosphorylated Hexim-1. Thus, where phosphorylated Hexim-1 is not detectable in a control, but is detectable in a subject sample, the subject sample cells are diagnosed as abnormal and tumorigenic. Similarly, if unphosphorylated Hexim-1 but not phosphorylated Hexim-1 is detectable in a subject sample, the subject sample cells are diagnosed as hyperplastic.

This disclosure further provides methods of monitoring a hyperplastic or cancerous condition in a subject by measuring the level of Hexim-1 in a sample from the subject. In one example, Hexim-1 levels in a sample from a subject are compared to Hexim-1 levels in a sample obtained from the same subject at an earlier time point. Elevated levels of Hexim-1 indicate that the hyperplastic or cancerous condition is worsening, while reduced levels of Hexim-1 indicate that the hyperplastic or cancerous condition is improving. By "worsening", it is meant the condition is becoming more advanced or severe, such as hyperplasia advancing to cancer, Stage I advancing to Stage II cancer, or relapse of a cancer that was in remission. By "improving", it is meant that the condition is reduced in severity, such as cancer going into remission, or reduction in or elimination of cancerous/hyperplastic cells.

In addition, this disclosure provides methods to determine the effectiveness of a cancer therapy in a subject, where elevated levels of Hexim-1 indicate that the cancer therapy is ineffective, and where reduced levels of Hexim-1 indicate that the cancer therapy is effective.

When multiple samples are obtained over time, such samples are obtained from a subject as determined by a physician. Samples may be obtained once every week, every two weeks, every four weeks, every six weeks, every month, every two months, every three months, or every four months or more. Samples may be obtained every four to six weeks, every one to two months, every one to three months, every one to four months, or every two to four months apart.

This disclosure further provides methods of treating cancer or hyperplasia, comprising administering to a subject in need thereof a therapeutically effective amount of Hexim-1, an activator of Hexim-1 expression or activity, or an inhibitor of Hexim-1 phosphorylation. This treatment can be combined with one or more additional cancer treatments.

This disclosure encompasses administration of Hexim-1 and/or one or more Hexim-1 activators as a cancer treatment. A "Hexim-1 activator" increases the expression, activity or function of Hexim-1. For example, a compound can act as a Hexim-1 activator by increasing or enhancing Hexim-1 expression or activity, or increasing the interaction of Hexim-1 with the pTEFb complex, resulting in an inhibition of RNA Pol II-mediated RNA elongation and reduction of cell proliferation. Examples of Hexim-1 activators include peptides, polypeptides, proteins, antibodies, small molecules, chemotherapeutic agents, and fragments, derivatives and analogs thereof, that increase or enhance the expression, activity or function of Hexim-1. An example of a Hexim-1 activator is the Cdk-inhibiting drug R547 (Hoffmann-La Roche).

Hexim-1 is inhibited by phosphorylation, particularly by tyrosine phosphorylation of the Y291 residue. Hexim-1 phosphorylation causes inhibition of Hexim-1 activity, for example, by preventing interaction of Hexim-1 and Cyclin T1, and/or by promoting Hexim-1 translocation out of the nucleus into the cytoplasm. Hexim-1 activity depends in part on the absence of Hexim-1 inhibition. Thus, an "inhibitor of Hexim-1 phosphorylation" can be an inhibitor of tyrosine phosphorylation, such as genistein, or a specific inhibitor that targets or protects the Y291 residue of Hexim-1 to prevent phosphorylation on this or other Hexim-1 residues.

As used herein, "treatment" refers to clinical intervention in an attempt to alter the disease course of the individual or cell being treated, and can be performed either for prophylaxis or during the course of clinical pathology. Therapeutic effects of treatment include without limitation, preventing occurrence or recurrence of disease, alleviation of symptoms, diminishment of any direct or indirect pathological consequences of the disease, decreasing the rate of disease progression, amelioration or palliation of the disease state, and remission or improved prognosis. For example, treatment of a cancer patient may be reduction of tumor size, elimination of malignant cells, prevention of metastasis, or the prevention of relapse in a patient whose tumor has regressed.

The term "cancer treatment" includes administration of any cancer agent including radioactive isotopes, and chemotherapeutic agents such as small molecule toxins or enzymatically active toxins of bacterial, fungal, plant or animal origin, including fragments and/or variants thereof. Any cancer treatment can be administered in combination with a therapeutically effective amount of Hexim-1 or an activator of Hexim-1 expression or activity. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *sapaonaria officinalis* inhibitor, and glucocorticoid and other chemotherapeutic agents, as well as radioisotopes. Cancer treatment further includes removal of cancerous tissue or cells by surgery, biopsy, or other means.

The recommended dosages of the cancer agents currently used for the prevention, treatment, and/or management of cancer can be obtained from any reference in the art including, but not limited to, Hardman et al., eds., Goodman & Gilman's *The Pharmacological Basis Of Therapeutics,* 10th ed, Mc-Graw-Hill, N.Y., 2001; and *Physician's Desk Reference* (60$^{th}$ ed., 2006), which are incorporated herein by reference in their entirety.

Hormones and the vascular growth factor VEGF increase Hexim-1 expression in cells. However, several cancer treatments involve inhibition or down-regulation of hormones, VEGF, and/or hormone or VEGF receptors. While these treatments show efficacy in treating cancer cells—hormone-sensitive cancers such as breast and prostate cancers often responding to hormone inhibition therapies, while many cancer types respond to anti-VEGF therapies—they can have the effect of reducing Hexim-1 expression. Therefore, administration of Hexim-1 or a Hexim-1 activator in combination with such treatments can be an effective means to maintain Hexim-1 cellular activity and further reduce cancer cell proliferation.

Hexim-1, a Hexim-1 activator, and/or an inhibitor of Hexim-1 phosphorylation can be administered to a patient by methods known in the art. For example, Hexim-1 expression may be upregulated in cells of a subject by gene therapy, such as by retrovirus-mediated integration of DNA encoding recombinant Hexim-1 into the genome of a patient.

Any type of cancer can be diagnosed, monitored and/or treated in accordance with the invention. Non-limiting examples of cancers that can be diagnosed, monitored and/or treated in accordance with the invention include: leukemias; lymphomas; multiple myelomas; bone and connective tissue sarcomas; brain tumors; breast cancer; adrenal cancer; thyroid cancer; pancreatic cancer; pituitary cancers; eye cancers; vaginal cancers; cervical cancers; uterine cancers; ovarian cancers; esophageal cancers; stomach cancers; colon cancers; rectal cancers; liver cancers; gallbladder cancers; cholangiocarcinomas; lung cancers; testicular cancers; prostate cancers; penile cancers; oral cancers; basal cancers; salivary gland cancers; pharynx cancers; skin cancers; kidney cancers; Wilms' tumor; bladder cancers. In one example, the cancer is prostate, breast, or pancreatic cancer. Similarly, the cell samples may be samples of any of the tissues described herein, such as prostate, breast, colon, pancreatic, lung, gastric, or bladder cells.

As used herein, the terms "subject" and "patient" are used interchangeably and refer to an animal, preferably a mammal such as a non-primate (e.g., cows, pigs, horses, cats, dogs, rats etc.) and a primate (e.g., monkey and human), and most preferably a human.

As used herein, the terms "therapeutically effective amount" and "effective amount" are used interchangeably to refer to an amount of a composition of the invention that is sufficient to result in the prevention of the development, recurrence, or onset of cancer and one or more symptoms thereof, to enhance or improve the prophylactic effect(s) of another therapy, reduce the severity and duration of cancer, ameliorate one or more symptoms of cancer, prevent the advancement of cancer, cause regression of cancer, and/or enhance or improve the therapeutic effect(s) of additional anticancer treatment(s).

A therapeutically effective amount can be administered to a patient in one or more doses sufficient to palliate, ameliorate, stabilize, reverse or slow the progression of the disease, or otherwise reduce the pathological consequences of the disease, or reduce the symptoms of the disease. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

For example, an "effective" therapy is able to achieve one, two or three or more of the following results, while an "ineffective" therapy achieves none of the following results: (1) an amelioration of cancer-related symptoms and/or quality of life; (2) a reduction or elimination in the cancer cell population; (3) a reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) the size of the tumor is maintained and does not increase or increases by less than 10%, or less than 5%, or less than 4%, or less than 2%, (10) an increase in the number of patients in remission, (11) an increase in the length or duration of remission, (12) a decrease in the recurrence rate of cancer, (13) an increase in the time to recurrence of cancer, or (14) a reduction in drug resistance of the cancer cells.

This disclosure also provides methods of screening for an activator of Hexim-1 expression, the including the steps of (i) providing a cell with a Hexim-1 promoter operably linked to a nucleic acid segment encoding an expressible marker; (ii) contacting said cell with a candidate substance; and (iii) assessing the expression of said marker, wherein an increase in expression of said marker, as compared to expression in a cell not contacted with said candidate substance, identifies said candidate compound as an activator of Hexim-1 expression.

As used herein the term "candidate compound" refers to any compound that can induce Hexim-1 expression. The candidate compound may be a protein or fragment thereof, a small molecule, or even a nucleic acid molecule. One may also acquire, from various commercial sources, small molecule libraries that are believed to meet the basic criteria for useful drugs in an effort to "brute force" the identification of useful compounds. Screening of such libraries, including combinatorally generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate compound identified by the present invention may be peptide, polypeptide, polynucleotide, small molecule inhibitors or any other compounds that may be designed through rational drug design starting from known inhibitors or stimulators.

The present disclosure is further illustrated by the following non-limiting examples.

EXAMPLES

Example 1: Hexim-1 Protein Expression is Up-Regulated in Hyperplasia and Adenocarcinoma of Prostate Cells Hexim-1 is a negative regulator of the transcription elongation complex (pTEFb) of RNA polymerase II (Pol II) transcription. The expression of Hexim-1 was evaluated by immunofluorescence analysis in a Human Prostate Cancer and Benign Prostate Hyperplasia (BPH) tissue array. Results revealed that Hexim-1 protein expression is completely absent in normal tissue sections (FIG. 1B) but levels are significantly enhanced during cellular growth and proliferation, in both BPH (FIGS. 1D and D1) and adenocarcinoma of the prostate (FIGS. 1F and F1).

Figure 1:
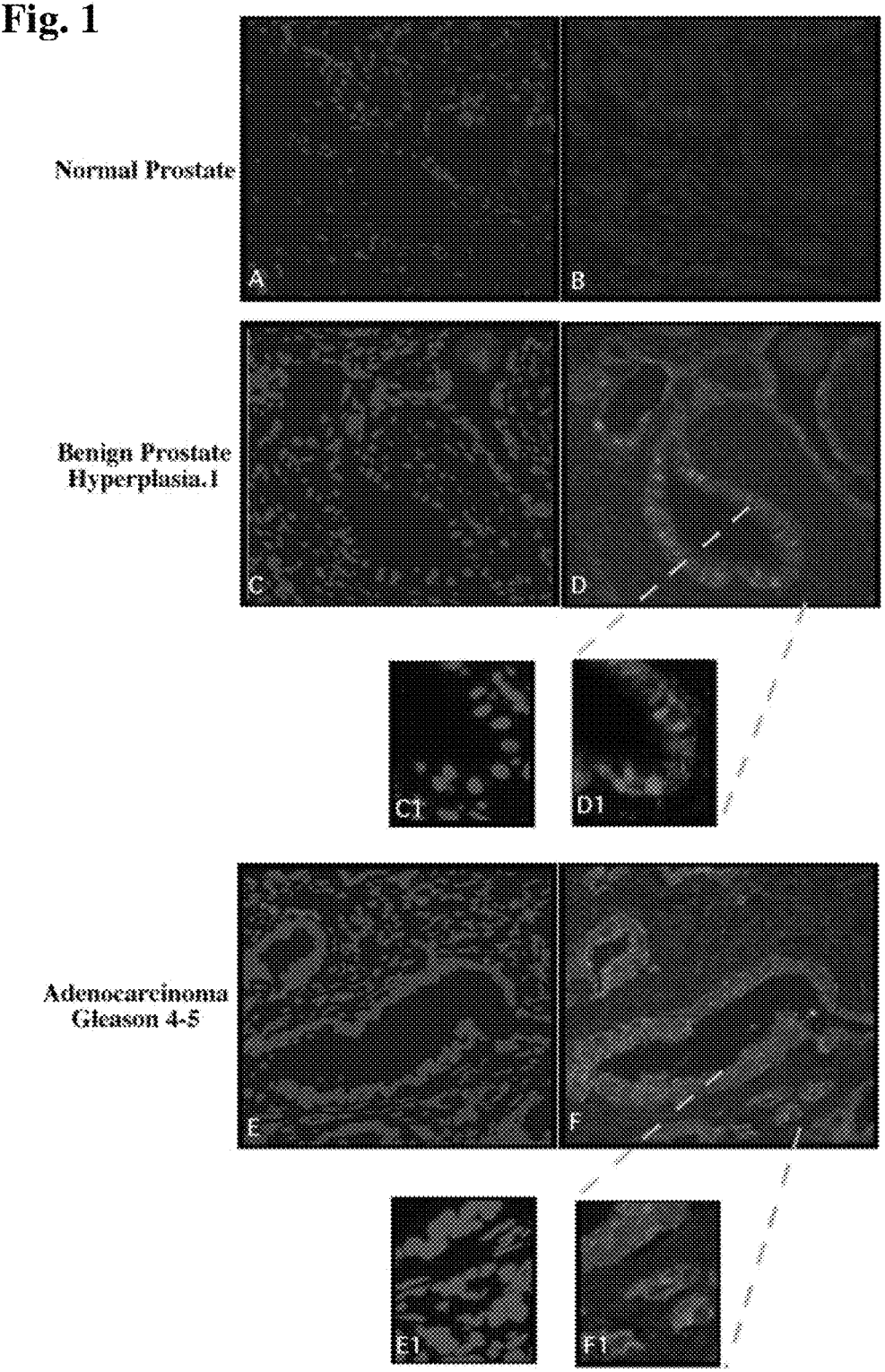
FIG. 1: Hexim-1 expression in human prostate tissue microarray. The expression of Hexim-1 was evaluated by immunofluorescence analysis in a human prostate cancer and benign prostate hyperplasia (BPH) tissue microarray. A, C, E: Identify the nuclear staining with DAPI as described in the Materials and Methods Section. B: Normal prostate. D: Benign prostate hyperplasia. C1 and D1 are insets to better show the nuclear localization of Hexim-1. F: Adenocarcinoma Gleason scores 4-5 respectively. E1, F1: insets to better show the cytoplasmic and nuclear localization of Hexim-1. The images were obtained at 20× magnification using a Nikon Microphot-SA microscope and SPOT Software version 4.6.

Additionally, cellular re-distribution of Hexim-1 was observed between benign-hyperplastic and tumorigenic prostate tissue. While there was an enhanced nuclear distribution of Hexim-1 during BPH (FIG. 1D1), Hexim-1 expression is compartmentalized to the cytoplasm of epithelial cells during adenocarcinoma of the prostate (FIG. 1F1).

Example 2: Testosterone and VEGF Increase Hexim-1 Expression in LNCaP Cells

Growth of prostate tissue is regulated by androgen and androgen regulated induction of growth factors in stromal cells. The prostate tumor tissue and cell lines such as LNCaP and PC3 are known to express receptors for vascular endothelial growth factor (VEGF), VEGFR-1 and R-2. VEGF expression is modulated by androgens and aggressiveness of the tumor is associated with angiogenesis.

Figure 2A:
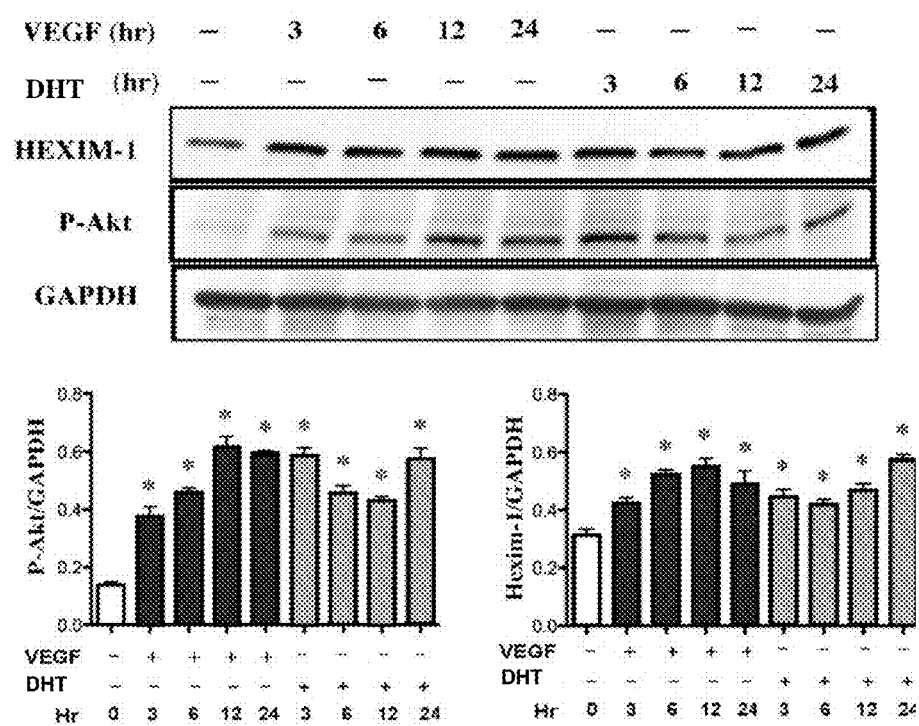
FIG. 2: Induction of Hexim-1 by DHT and VEGF.

In this example, to determine the responsiveness of Hexim-1 to androgen and VEGF in the epithelial prostate LNCap cell line, LNCap cells were treated with VEGF (10 ng/mL) or 10 nM dihydrotestosterone (DHT) for 3, 6, 12 and 24 hours, with the change in expression of Hexim-1 protein evaluated by Western blot. Results indicated that Hexim-1 protein levels were induced by both agonists, DHT and VEGF. These results can be seen in FIG. 2A. FIG. 2A is indicative of the expression of phosphorylated Akd (pAkt) in LNCaP upon induction with DHT or VEGF and observes that p-Akt levels correlated with the increased Hexim-1 expression.

FIG. 2A illustrates the epithelial prostate LNCaP cell line which was treated with VEGF (10 ng/ml) or 10 nM dihydrotestosterone (DHT) 10 nM for 3, 6, 12 and 24 hr. Protein extracts were obtained from each time point and the changes in the protein expression of Hexim-1, p-Akt and GAPDH evaluated by Western blot. The histogram indicates the ratio between p-AKT and GAPDH and the ratio of Hexim-1 to GAPDH as obtained by densitometry analysis of the Western blots. Data are expressed as means±SE of 4 independent experiments. P-Akt *P<0.05 compared control vs. VEGF and DHT treatment. Hexim-1 expression, *P<0.05 compared control vs. VEGF and DHT treatment.

Figure 2B:
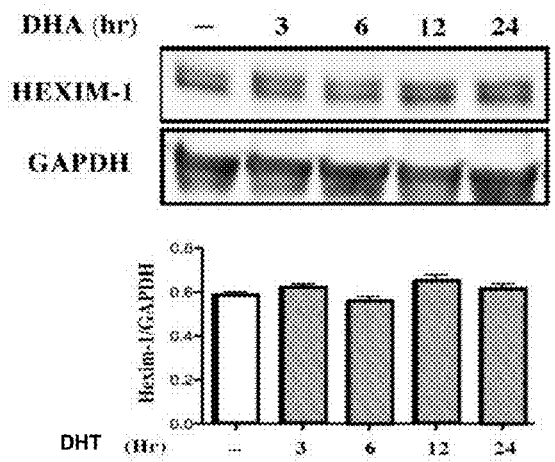

In androgen independent cell line PC3, Hexim-1 levels were not changed upon treatment with DHT, as can be seen in FIG. 2B. In FIG. 2B, PC3 cells were treated with 10 nM DHT for indicated times, cells were collected and cellular extracts were prepared and analyzed for Hexim-1 and GAPDH. The histogram indicates a ratio between Hexim-1 and GAPDH. Data are expressed as means±SE of 3 independent experiments. No significant induction was observed.

Example 3: Hexim-1 Protein Levels are Up-Regulated in a Mouse Model of Prostate Adenocarcinoma TRAMP In order to evaluate the role of Hexim-1 in the established TRAMP mouse model, TRAMP mice were obtained from Jackson Laboratory. All animal experiments were conducted in accordance with the Guide for the Care and Use of Laboratory Animals published by the US National Institutes of Health (NIH Publication No. 85-23, revised 1996).

The Hexim-1 gene is highly homologous between human and mice and is characterized by a single exon with conserved regulatory regions. The murine Hexim-1 homolog is called CLP-1; this disclosure refers to CLP-1 mice interchangeably as "CLP-1" and "Hexim-1" mice.

TRAMP mice harbor the Transgenic Adenocarcinoma of the Mouse Prostate (TRAMP); PB-Tag Line 8247 transgene (strain information available from Jackson Laboratories, JAX Mice Database, C57BL/6-Tg(TRAMP)8247Ng/J, Strain Information). Mice hemizygous for the TRAMP transgene develop progressive forms of prostate cancer with distant site metastasis and exhibit various forms of disease from mild intraepithelial hyperplasia to large multinodular malignant neoplasia. TRAMP hemizygotes can exhibit prostatic epithelial neoplasia (PIN) by 12 weeks of age. Tumors, as well as differentiated adenocarcinoma, can arise by 24 weeks of age, mostly in the dorsal and lateral lobes of the prostate. By 30 weeks of age, most hemizygous mice will display evidence of metastatic spread to the lymph nodes and/or lungs, phylloides appearance of some tumors, and seminal vesicle invasion. Tumors exhibit elevated levels of nuclear TRP53 and decreased androgen receptor expression.

Tissue Preparation:

Prostate tissue from TRAMP (n=10) and TRAMP×Hexim-1+/− (n=12) were obtained and fixed in 10% buffered formalin for 24 hr, followed by washing in phosphate buffer saline (PBS) and transferred to 30% sucrose/PBS overnight. The tissue was mounted in M-1 embedding matrix and maintained at −80° C.

Immunofluorescence:

MaxArray™ human prostate microarray slides (Zymed) containing normal, adenocarcinoma of the prostate at Gleason score ranging from 2 to 5 (n=20), benign prostate hyperplasia (BPH) (n=20) tissues were subjected to Citrate-EDTA antigen retrieval protocol. Tissue sections were deparaffinized twice in xylene for 5 min followed by hydration in 100% ethanol for 3 min, 95% ethanol for 3 min and 80% ethanol for 1 min. Then slides were incubate in citrate-EDTA buffer (10 mM citric acid, 2 mM EDTA, 0.05% Tween pH 6.2) at 95-100° C. for 20 min. Slides were remove and allowed to cool for 20 min, then washed twice in PBS contain 0.01% Tween. The slides were incubated with 2% fetal bovine serum (FBS) in PBS at room temperature for 2 hr, and incubated with rabbit anti-Hexim-1 (Abcam) overnight at 4° C. in a humidified chamber. The slides were washed in PBS followed by incubation with secondary Alexa-anti-rabbit-596 (10 µg/ml) in PBS and 2% FBS for 1 h at room temperature. Slides were washed three times in PBS followed by mounting in DAPI (nuclear staining) anti fade from Invitrogen. All images were captured using a digital camera and Axiovision 3.1 software (Carl Zeiss Inc.).

Western Blot and Antibodies:

Prostate tissues from wild type, heterozygous Hexim-1, TRAMP and TRAMP×Hexim-1 mice (n=3 in each group) were homogenized in lysis buffer (50 mM Tris-HCl pH 8.0, 10 mM $MgCl_2$, 120 mM NaCl, 0.5% Nonidet P-40, 5 mM dithiothreitol, 2.5 mM $MnCl_2$, protease inhibitors and RNAsin 40 U/ml (Promega). Proteins were separated on a 7.5% SDS/polyacrylamide gel and transferred to nitrocellulose membrane, Nitropure (Micron Separations, Westboro, Mass.) Blots were probed with antibodies PCNA (sc-56) and GAPDH (sc-25778) from Santa Cruz Biotechnology, Hexim-1 (Abcam) and developed according to the Chemiluminiscence protocol (Amersham). Anti Androgen receptor (Abcam), phosphoserine-2 Pol II (Abcam), anti phosphoserine-81 androgen receptor (Millipore), anti-phospho-serine-208 and anti-threonine-179 Smad3 from Dr. Fang Liu at the Center for Advanced Biotechnology and Medicine, Rutgers N.J.

Cell Culture and Stable Cell Line Generation:

TRAMP cells were grown in DMEM-high glucose media containing FBS, Pen/Strep (Invitrogen) and 3.7 g/L $NaHCO_3$. TRAMPC2 cells were transfected with the linearized HEXIM-1 containing the Neomycin-resistant cassette (Huang F, et al. *Mech Dev* 2004; 121:559-572). Neo-transfected cells were selected in medium with neomycin (250 µg/ml) The recombinants were identified by PCR, as previously described (Huang F, et al. *Mech Dev* 2004; 121:559-572) and maintained with medium containing neomycin (250 µg/ml).

Transient Transfection and Luciferase Assay:

The transfection assay was performed as previously described (21). Essentially, the smooth muscle 22 alpha promoter and luciferase gene as reporter with 10 ng of thymidine kinase promoter-driven *Renilla* luciferase-thymidine kinase vector were transfected in TRAMP-C2 or TRAMP-C2-Hexim-1+/− cell lines. The expression vectors pSmad3 carrying the wild type and the pSMLSmad3 (22) carrying a substitution mutation of the serine/threonine residues in the linker region were co-transfected with the pSM22Luc reporter (kindly provided by Li Li Ph.D. at the Center for Molecular Medicine & Genetics-Wayne State University). After 24 hr the transfected cells were maintained for 12 h in serum free medium, then TGFβ (5 ng/ml) was added and the cells collected the indicated time points. Luciferase assays were performed with the dual luciferase assay kit (Promega, Madison, Wis.).

Statistical analysis was performed using the software GraphPadPrism5. The results are represented as mean±S. D. For statistical analyses One-way-ANOVA and Bonferroni post-test were used. Values of p<0.05 were considered as significant.

Figure 3A:
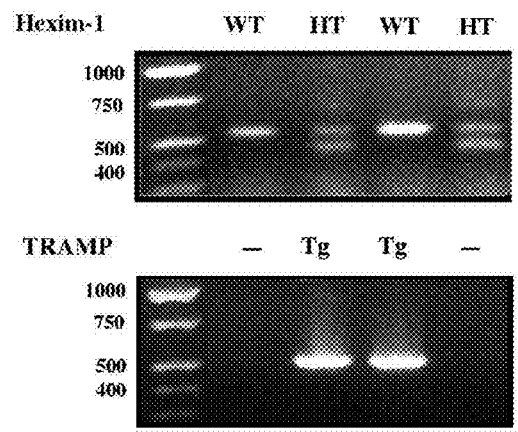
FIG. 3: Characterization of TRAMP/Hexim-1 genetic background. A: Genomic DNA was analyzed for CLP-1 background using the forward primer 5'-AACCTCCTCTC-CTTGCGCACCAACTC-3' (SEQ ID NO: 1), the reverse primer 5'-TACTGTCCTCCTTGGGCACCCGTTCC-3' (SEQ ID NO: 2), and the neomycin resistance gene reverse primer 5'-TACCGGTGGATGTGGAATGTGTGCGA-3' (SEQ ID NO: 3) under the following conditions: 95° C.×3 min, 94° C.×30 sec, 65° C.×1 min, and 72° C.×30 sec, for 35 cycles. Same isolated tail-DNA was used to determine the TRAMP genotype with the following primers: oIMR7084 5'-GCGCTGCTGACTTTCTAAACATAAG-3' (SEQ ID NO: 4); oIMR7085 5'-GAGCTCACG TTA AGTTTTGAT-GTGT-3' (SEQ ID NO: 5) under the following conditions: 95° C.×3 min, 94° C.×30 sec, 60° C.×1 min, and 72° C.×30 sec, for 35 cycles. B: Total protein extracts were obtained from prostate tissue of TRAMP and TRAMP+/−; Hexim-1+/− mice to evaluate the expression of Hexim-1 during the progression of PCA. Expression of proliferating-cell nuclear antigen (PCNA) was used as an internal positive control of increased proliferation. GAPDH was used as loading control. Representative Western blot with duplicate samples from the transgenic mice is shown. WT=C57BL6. HT=C57BL6; Hexim-1+/−. TRAMP-WT=C57BL/6; TRAMP. TRAMP-HT=C57BL/6; TRAMP; Hexim-1+/−. C: Ratio of Hexim-1 to GAPDH expression. Data are expressed as mean+/−SE of four independent experiments. Hexim-1 expression, *P<0.05 TRAMP (T/WT) versus TRAMP/Hexim-1+/− (T/HT). D: Ratio of PCNA to GAPDH expression. Data are expressed as mean+/−SE of four independent experiments. PCNA expression, *P<0.05 TRAMP (T/WT) versus TRAMP/Hexim-1+/− (T/HT).

The TRAMP mice used herein were a cross of C57BL/6-Tg (TRAMP) with C57BL/6J-Hexim-1 heterozygous mice. Genomic DNA was analyzed for CLP-1/Hexim-1 background using the forward primer 5'-AACCTCCTCTC-CTTGCGCACCAACTC-3' (SEQ ID NO: 1), the reverse primer 5'-TACTGTCCTCCTTGGGCACCCGTTCC-3' (SEQ ID NO: 2), and the Neomycin resistance gene reverse primer 5'-TACCGGTGGATGTGGAATGTGTGCGA-3' (SEQ ID NO: 3) under the following conditions: 95° C.×3 min, 94° C.×30 s, 65° C.×1 min, and 72° C.×30 sec, for 35 cycles (FIG. 3A). FIG. 3A is PCR genotyping of tail DNA from wild type mice for Hexim-1 (+/+) (WT) and for Hexim-1 heterozygous mice (+/−). PCR primers were chosen to generate a 457 bp product diagnostic of the wild-type Hexim-1 gene and a 383 bp product diagnostic of a mutated allele. A heterozygous Hexim-1 background produces a higher band (457 bp) and a lower band (383 bp).

Same isolated tail-DNA was used to determine the TRAMP genotype with the following primers, oIMR7084 5'-GCGCTGCTGACTTTCTAAACATAAG-3'(SEQ ID NO: 4); oIMR7085 5'-GAGCTCACGTTAAGTTTTGAT-GTGT-3' (SEQ ID NO: 5) under the following conditions: 95° C.×3 min, 94° C.×30 s, 60° C.×1 min, and 72° C.×30 sec, for 35 cycles. TG (transgenic) lanes represent the PCR product amplifying the fusion transgene probascin-T-antigen incorporated in the mice genome of transgenic TRAMP mice only, generating a product of about 500 bp.

Figure 3B:
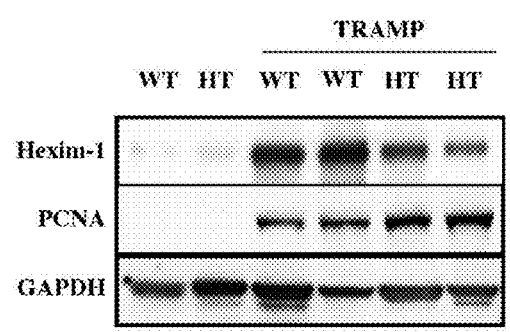
Figure 3C:
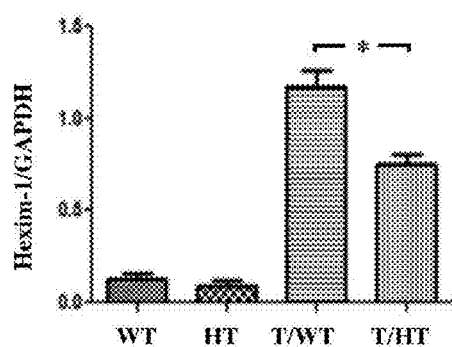
Figure 3D:
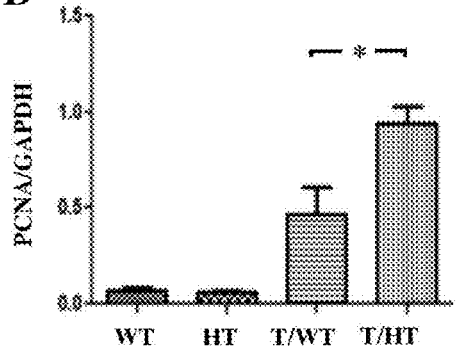

Hexim-1 null mice are embryonic lethal and the C57BL/6J-Hexim-1+/− hemizygous mice are viable but susceptible to stress. In FIG. 3B, total prostate protein extracts were obtained from TRAMP and TRAMP×Hexim-1+/− mice to evaluate the expression of Hexim-1 during the progression of PC. Proliferating-cell nuclear antigen (PCNA) expression was used as an internal positive control of increased proliferation. GAPDH was used as loading control. Representative Western Blot with duplicate samples from the transgenic mice is shown. WT=C57BL6. HT=C57BL6; Hexim-1+/−. TRAMP-WT=C57BL/6; TRAMP. TRAMP-HT=C57BL/6; TRAMP; Hexim-1+/−. As illustrated in FIG. 3B, the expression of Hexim-1 observed in prostate tissue in wild type and heterozygous mice is negligible; however, C57BL/6-TRAMP and C57BL/6-TRAMP-Hexim-1+/− revealed an increase in levels of Hexim-1 protein expression during prostate tumor progression with a larger increase in C57BL/6-TRAMP. FIG. 3C indicates the ratio of Hexim-1 to GAPDH. FIG. 3D indicates the ratio of PCNA to GAPDH. Data are expressed as mean±SE of 4 independent experiments: FIG. 3C, Hexim-1 expression, *P<0.05 TRAMP vs. TRAMP/Hexim-1+/−. FIG. 3D, PCNA expression, *P<0.05 TRAMP vs.TRAMP/Hexim-1+/−.

Since transcription elongation is regulated by Cdk9 mediated serine phosphorylation at the serine residue 2 in the carboxyl terminus of RNA polymerase Pol II, an analysis was done to determine whether the decreased levels of Hexim-1 protein expression observed in the bigenic (TRAMP+/−; Hexim-1+/−) mice correlated with an increased Serine 2 phosphorylation activity. As shown in FIG. 4A, there was a significant increase in serine-2 phosphorylation in the prostate tumor of both transgenic mice models. In FIG. 4A, total prostate protein extract obtained from TRAMP and TRAMP×Hexim-1+/− mice were used to evaluate the Cdk9 dependent Serine-2 phosphorylation activity. Total RNA Pol II expression was used as loading control. Representative Western Blot with duplicate samples from the transgenic mice is shown. C57BL6 (WT), C57BL6-Hexim-1+/− (HT), C57BL/6-TRAMP (TRAMP-WT) and C57BL/6-TRAMP×Hexim-1+/− (TRAMP-HT).

Cellular extracts from prostate tissue of wild type, Hexim-1 heterozygous, TRAMP mice and TRAMP-Hexim-1 mice were immunoprecipitated with androgen receptor antibody and analyzed for co-immunoprecipitation with Cdk9. As shown in FIG. 4B, extracts from wild type and heterozygous mice failed to reveal any interaction between Cdk9 and androgen receptor (AR). In FIG. 4B, the role of Cdk9 activity as a serine kinase protein on the androgen receptor was evaluated by immunoprecipitation. Upper panel shows an increased interaction between Cdk9 and the androgen receptor in extract from the bigenic mice. Middle panel revealed increased serine phosphorylation of the androgen receptor in the bigenic mice. Lower panel represents the loading control as evaluated by the expression levels of total androgen receptor. C57BL6 (WT), C57BL6-Hexim-1+/− (HT), C57BL/6-TRAMP (TRMP-WT) and C57BL/6TRAMP×Hexim-1+/− (TRMP-HT).

In both transgenic mice models of prostate cancer, Cdk9 was associated with androgen receptor, however, enhanced AR-Cdk9 interaction was observed in the bigenic mice. The functional consequence of this interaction was further analyzed in terms of serine phosphorylation of the AR. As shown in FIG. 4B, the serine phosphorylation of AR is significantly increased.

Example 4: Hexim-1 Modulates the TGFβ/SMADs Signaling Pathway

Figure 5B:
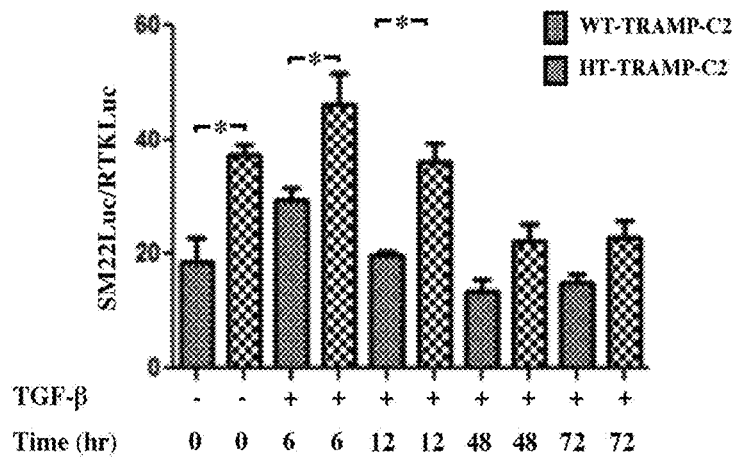
Figure 5C:
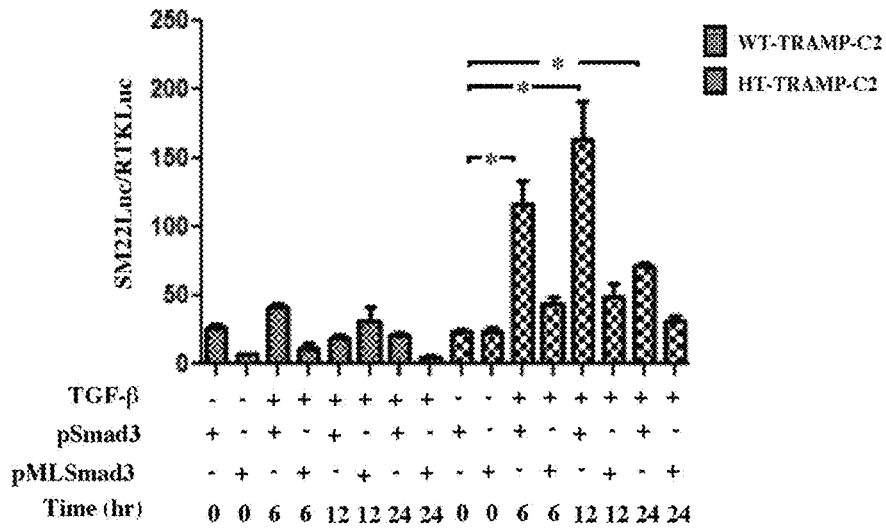

In order to further establish that Hexim-1 protein expression levels modulate the TGFβ/SMADs signaling pathway during prostate cancer, the inventors used the mouse TRAMP-C2 cell line (27) to disrupt one copy of the Hexim-1 gene generating a TRAMP/HEXIM+/− heterozygous cell line, HT-TRAMP-C2. As observed in FIG. 5A, PCR and Western blot of the heterozygous TRAMP-C2 cell line revealed the integration of the neo-cassette in the Hexim-1 heterozygous cell line and a decreased Hexim-1 protein expression levels respectively. Then, the inventors evaluated whether changes in Hexim-1 protein expression alter the Cdk9 dependent TGF-β/SMAD signaling pathway. It has been previously reported that the smooth muscle 22 alpha promoter is regulated by TGF-β (28), and increased expression of SM22 alpha correlates with cancer (29), and metastasis (30). To test the role of Hexim-1 in TGFβ signaling, the inventors determined SM22Alpha promoter-Luciferase activity in both TRAMP cell lines. As shown in FIG. 5B, WT-TRAMP-C2, and HT-TRAMP-C2 (neo) cells transiently transfected with the promoter SM22alphaLuciferase followed by treatment with TGF-β for the indicated time points, revealed a significantly increased SM22alpha Luciferase activity in HT-TRAMP-C2 cells. Further support for the role of Hexim-1 as a modulator of TGF/Smad3 activity was obtained by co-transfection of SM22alpha Luciferase with the expression vector of wild type Smad3 (pSmad3) or a pMLSmad3 which carries substitution mutations of the serine and threonine residues in the polinker region of Smad3. FIG. 5C shows that upon treatment of co-transfected cells with TGF-β, a significant increase in the SM22alpha reporter activity in HT-TRAMP-C2 cells was observed only in the presence of pSmad3.

Example 5: TRAMP×Hexim-1 Bigenic Mice Develop Aggressive Prostate Cancer

Figure 6A:
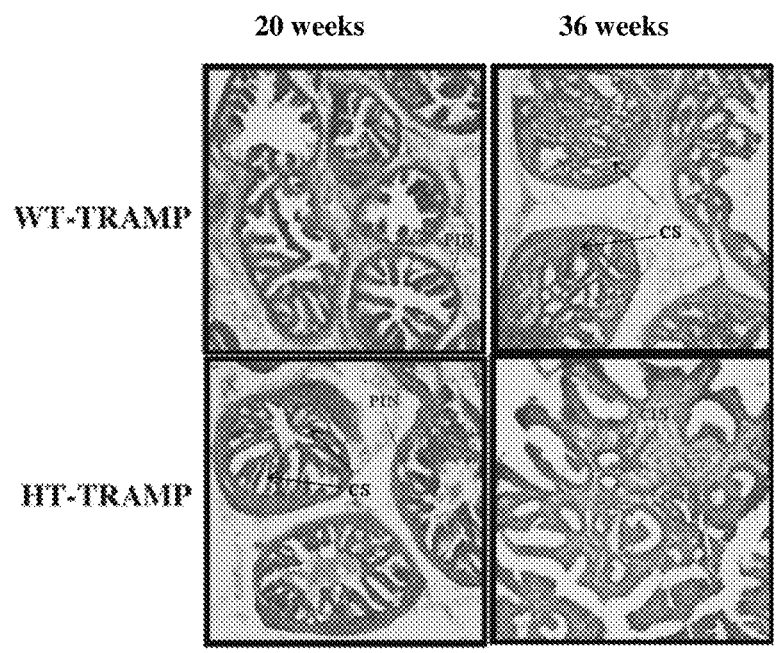

Further characterization of bigenic mice and the progression of PC was obtained by histological examination of the prostate in wild type, heterozygous, TRAMP and TRAMP×Hexim-1+/− mice. As seen in FIG. 6A, the histological analysis from 20 and 36 weeks revealed changes unique to TRAMP or TRAMP/Hexim-1+/−. In FIG. 6A, Hematoxylin-Eosin staining of anterior prostate of WT, HT, TRAMP-WT and TRAMP-HT mice at 24 and 36 weeks of age is shown. A high grade prostatic intraepithelial neoplasia (High PIN), carcinoma in situ (CIS) with extensive pleomorphism and cribiform structures and invasive carcinoma in TRAMP×Hexim-1+/− mice at earlier time frame than in the TRAMP background was observed.

At 20 weeks TRAMP mice revealed low grade prostatic intraepithelial neoplasia (Low PIN) and high grade prostatic intraepithelial neoplasia (High PIN), however, TRAMP×Hexim-1 revealed primarily carcinoma in situ (CIS) as extensive pleomorphism and cribiform structures as well as an increase in smooth muscle proliferation. Later, at 36 weeks, mainly carcinoma in situ in TRAMP mice was observed but TRAMP/Hexim-1+/− shows a carcinoma with minimal glandular structures.

Figure 6B:
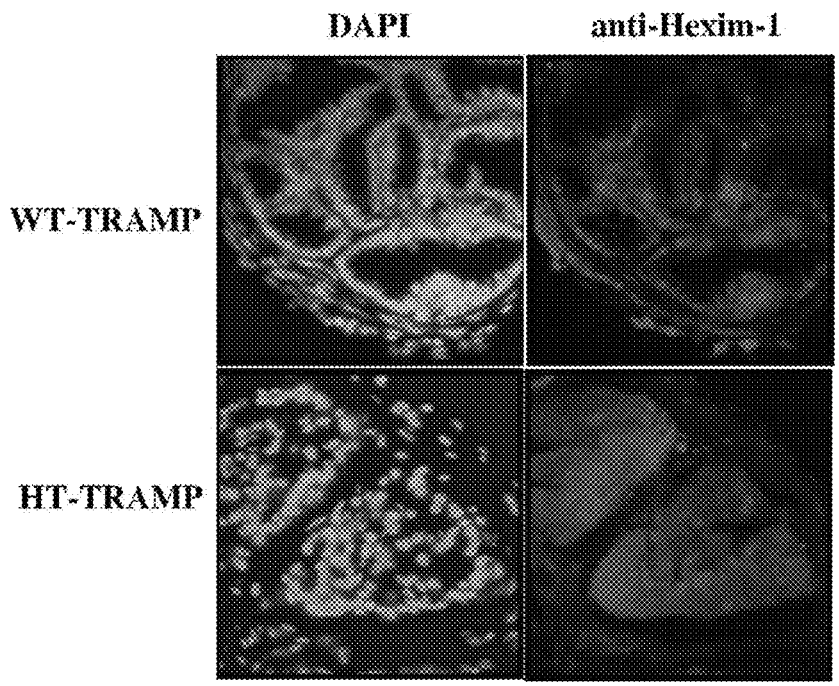

The cytoplasmic cellular re-distribution of Hexim-1 protein observed in adenocarcinoma of the prostate (as discussed in regard to FIG. 1), was also observed in high PIN of a sample from TRAMP/Hexim-1+/− as shown in FIG. 6B. In FIG. 6B, the images were obtained at 20× magnification, expression of Hexim-1 was evaluated by immunofluorescence in C57BL/6-TRAMP and C57BL/6-TRAMP×Hexim-1+/− sections. WT-TRAMP revealed the nuclear staining of Hexim-1 protein as confirmed by DAPI. However, Hexim-1-HT-TRAMP shows uniform distribution of Hexim-1 protein in the nuclei and cytoplasm. DAPI staining identifies the nuclear localization of the High PIN epithelium. The images were obtained at 40× magnification using a Nikon Microphot-SA microscope and SPOT Software version 4.6.

As is shown in FIG. 6B, Hexim-1 protein expression was localized in the nuclei in sections from TRAMP mice, however, in the bigenic mice Hexim-1 expression was observed in the nuclei and the cytoplasmic compartment.

Translocation from the nucleus to the cytoplasm is a consequence of posttranslational modification of Hexim-1 via tyrosine phosphorylation of Hexim-1 residue Y291. Hexim-1 is an inhibitor of cell proliferation, and is up-regulated in response to disordered proliferation, an element of cancer and pre-cancerous states. In order for the cancer to continue or progress, natural inhibitors of cell proliferation such as Hexim-1 must be overcome. One way to overcome an inhibitor of cellular proliferation is to change the cellular location of the inhibitor. Hexim-1 is an inhibitor of proliferation when localized to the nucleus, however, in the cytoplasm Hexim-1 cannot stop proliferation. The Y921 residue is key in the interaction of Hexim1 and cyclinT1. When cyclinT1 is interacting with Hexim-1, cdk9 cannot promote transcription, and RNA polymerase stalls. The phosphorylation of the Y291 residue is mediated by Jak2 kinase. Heterozygous TRAMP mice do not express suppressor of cytokine signaling 3 (SOCS3), the inhibitor of Jak2. Thus, in the TRAMP background, absence of SOCS3 triggers an enhanced Jak2 activity, with increased Hexim-1 translocation, less inhibition of proliferation and more aggressive cancer.

Due to the discovery of these significant molecular events mediated by Hexim-1, Hexim-1 is herein identified as a significant tool for diagnosis and treatment of cancers, including prostate cancer. Diagnosis is based on identification of increases in the expression of Hexim-1; tyrosine phosphorylation of the described specific residues on Hexim1; molecules (including, but not limited to, anti-P1Hexim1 and P2Hexim1 antibodies) that can specifically recognize the Y291 epitope; or any form of tracing Hexim-1 expression and/or Hexim-1 epitopes. Because inactivation of Hexim-1, such as by Jak2 mediated phosphorylation, is now identified as a step in the progression of cancer, inhibitors of tyrosine phosphorylation and specific inhibitors that target the Y291 residue are also herein identified as means to inhibit cancer, including prostate, breast, colon, pancreatic, lung, gastric, or bladder cancer.

Hexim-1 is clearly a sensor for cellular proliferation because in absence of deregulated growth observed in normal tissues, there is little Hexim-1 expression. However, during cancer, there is a significant increase in Hexim-1 expression.

In addition to increases in Hexim-1 expression during cancer progression, posttranslational modification via phosphorylation on Hexim-1 appears during cancer stages only, while absent in benign hyperplasia. Therefore, phospho-specific anti Hexim-1 markers, such as Hexim1 antibodies, are essential to distinguish between elevated but regulated growth (benign hyperplasia) and abnormal deregulated growth such as adenocarcinoma and metastasis.

Prostate cancer is used here as a model for cancer development (FIG. 7). The morphological transition undergone in the prostate is parallel with a significant increase in Hexim-1 expression, a direct inhibitor of the cyclin dependent kinase 9 (Cdk9). In absence of Hexim-1 inhibition, Cdk9 serine kinase activity targets the carboxyl terminus of RNA Pol II, the androgen receptor and the TGFβ-1 pathway. All the Cdk9 targets identified play a significant role during the progression of prostate cancer. Therefore, as a natural feedback loop the early phase of proliferation of the prostate, the expression of Hexim-1 is significantly increased, resulting in an initial regulated Cdk9 activity, or regulated proliferation. The previously identified role of Hexim-1 as an inhibitor of cellular proliferation (Ouchida, R., et al., *Genes Cells* 8:95-107 (2003)) correlates with the increased levels of Hexim-1 observed in this study as a necessary element to regulate cell proliferation in the prostate and in other tissues with metastatic potential.

Example 6: Example of Claimed Methods as they would be Practiced

In this example, the methods of the claims are discussed as they would be practiced in a clinical setting using the example of prostate diagnosis. Although the method relying on urine samples and the method relying on prostate cell samples do not need to be used together or simultaneously, in this example they are discussed as being used sequentially.

Initially a subject, in this case a human, goes to a suitable medical facility. The person then provides a urine sample in a suitable vessel. The vessel is then transported to a suitable laboratory facility for measurement of Hexim-1 levels in the urine. The level of Hexim-1 is then measured in the urine sample using enzyme linked immunosorbent assay (ELISA) or a PCR procedure. Since, in this example, levels of Hexim-1 are detectable in the urine sample, the person is assigned to an abnormal group. The abnormal group means that the person's prostate is either hyperplastic or tumorigenic.

Once the person learns they have been placed in the abnormal group, they can proceed with the method of diagnosing prostate cancer. Initially, a sample of prostate cells is taken from the patient in a suitable medical facility by a biopsy procedure. The prostate cells are then transported to a suitable laboratory facility for measurement of Hexim-1 levels in the nucleus and cytoplasm of prostate cells. Once at the laboratory facility, the level of Hexim-1 expression in both the nucleus and the cytoplasm of the prostate cells is measured using an immunohistochemistry procedure which is more fully described in the previous examples. Since, in this example, Hexim-1 levels are detectable in the nuclei of the prostate cells and not the cytoplasm of the prostate cells, the person is diagnosed as having prostate hyperplasia. Based on this assignment, the person will know that their prostate is hyperplastic but not tumorigenic and the proper course of treatment can be determined with the aid of a health care provider.

Example 7: Example of Claimed Methods as they would be Practiced

In this example, Hexim-1 is measured by a modified electrochemical immunosensor assay (EIA) for simultaneous detection of Hexim-1 and the phosphorylated Hexim-1 proteins P1-Hexim-1 and P2-Hexim-1 via a multiplexed EIA that combines an enzyme-label amplification approach with an electric field driven acceleration method.

Materials and Methods.

Antibodies to Hexim-1, P1-Hexim-1, P2-Hexim-1, and other reagents are commercially or publicly available Immunosensor array is fabricated according to Du, et al., *Anal. Chem.* 83:6580-6585 (2011), adhering anti-Hexim-1, anti-P1-Hexim-1, or anti-P2-Hexim-1 antibodies to one electrode each. Electrochemical analysis and immunosensor readings are conducted using standard equipment. Simultaneous immunoassay is conducted according to Du, et al., above, using HRP as a detecting enzyme, and gold nanorods (AuNR) as a carrier to co-immobilize HRP, for detection of antibodies that specifically recognize either Hexim-1, or P1-Hexim-1 or P2-Hexim-1 in a patient sample. It will be evident to one of ordinary skill in the art that variations to the exemplary immunoassay herein described can be instituted without altering the principles of the invention, and are encompassed within this disclosure of the invention.

In this example following the procedure of Du, et al., above, the following complexes can be obtained: HRP/anti-Hexim-1-AuNR, HRP/anti-P1-Hexim-1-AuNR, and/or HRP/anti-P2-Hexim-1-AuNR. A positive driving potential is applied to accelerate the transport of negatively charged Hexim-1 proteins (Hexim-1, P1-Hexim-1, and P2-Hexim-1) to the electrode surface, followed by application of a low negative driving potential that accelerates the transport of positively charged HRP/anti-Hexim-1-AuNR, HRP/anti-P1-Hexim-1-AuNR. HRP/anti-P2-Hexim-1-AuNR bioconjugates form the following specific immuno-sandwiches: anti-Hexim-1/Hexim-1 protein/HRP/anti-Hexim-1-AuNR, or anti-P1-Hexim-1/P1Hexim-1 protein/HRP/P1-anti-Hexim-1-AuNR, or anti-P2-Hexim-1/P2Hexim-1 protein/HRP/anti P2-Hexim-1-AuNR adhered to each working electrode (FIG. 8). Measurement of activity at each electrode by voltammetry indicates the presence and amount of Hexim-1, P1-Hexim-1, and P2-Hexim-1 in a sample.

Utilizing the above procedure in the diagnosis of a blood or urine sample, the absence of detectable levels of any of Hexim-1, P1-Hexim-1, or P2-Hexim-1 indicates that the subject has normal tissues, while the presence of detectable levels of Hexim-1, P1-Hexim-1, or P2-Hexim-1, where detectable levels are indicated by measurement of current at 0.2 to 1 µA at a specific redox peak, such −0.256 V or −0.238 V, indicates tissue abnormality, such as prostate, breast, colon, pancreatic, lung, gastric, or bladder hyperplasia. Further, elevated levels of Hexim-1, P1-Hexim-1 and/or P2-Hexim-1, where elevated levels are indicated by measurement of current at or above 1 µA at a specific redox peak, such as −0.256 V or −0.238 V, indicates cancer.

What is claimed is:

1. A method of diagnosing and treating prostate cancer in a patient, which comprises:
   obtaining a sample from a human patient;
   detecting whether Hexim-1 is present in the sample by contacting the sample with an antibody of Hexim-1;
   diagnosing the patient with prostate cancer when a level of Hexim-1 in the sample is detected; and
   administering to the patient a therapeutically effective amount of Hexim-1, an activator of Hexim-1 expression or activity, or an inhibitor of Hexim-1 phosphorylation.

2. The method of claim 1, wherein the sample is a blood, urine, or tissue sample.

3. The method of claim 1, wherein levels of Hexim-1 are detected by immunohistochemistry.

4. The method of claim 1, wherein levels of Hexim-1 are detected by electrochemical immunosensor assay (EIA), enzyme-linked immunosorbent assay (ELISA), or polymerase chain reaction (PCR).

5. The method of claim 1, wherein an antibody that specifically binds Hexim-1 is adhered to an electrode, wherein HRP and gold nanorods (AuNR) for detection of Hexim-1 antibodies are added to an assay, wherein a positive driving potential is applied to the assay prior to application of a low negative driving potential to the assay, wherein Hexim-1 binds to a working electrode and a level of Hexim-1 is measured by voltammetry.

* * * * *

UNITED STATES PATENT AND TRADEMARK OFFICE
CERTIFICATE OF CORRECTION

| | |
|---|---|
| PATENT NO. | : 9,789,159 B2 |
| APPLICATION NO. | : 14/006406 |
| DATED | : October 17, 2017 |
| INVENTOR(S) | : Manya Dhar-Mascareno and Eduardo Mascareno |

It is certified that error appears in the above-identified patent and that said Letters Patent is hereby corrected as shown below:

In the Specification

At Column 1 at Line 9 after the term "entirely.", insert:
--STATEMENT REGARDING FEDERALLY SPONSORED RESEARCH
This invention was made with government support under CA169984, and GM008722 awarded by the National Institutes of Health. The government has certain rights in the invention.--

Signed and Sealed this
Twenty-sixth Day of March, 2024

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: forward primer

<400> SEQUENCE: 1
aacctcctct ccttgcgcac caactc                                        26

<210> SEQ ID NO 2
<211> LENGTH: 26
<212> TYPE: DNA
<213> ORGANISM: Artificial Sequence
<220> FEATURE:
<223> OTHER INFORMATION: reverse primer

<400> SEQUENCE: 2
tactgtcctc cttgggcacc cgttcc                                        26

<210> SEQ ID NO 3
<211> LENGTH: 26
<212> TYPE: DNA
<213> ORGANISM: Artificial Sequence
<220> FEATURE:
<223> OTHER INFORMATION: reverse primer

<400> SEQUENCE: 3
taccggtgga tgtggaatgt gtgcga                                        26

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
gcgctgctga ctttctaaac ataag                                         25

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
gagctcacgt taagttttga tgtgt                                         25

<210> SEQ ID NO 6
<211> LENGTH: 7
<212> TYPE: PRT
<213> ORGANISM: Homo sapiens
```

```
<400> SEQUENCE: 6

Tyr Ser Pro Thr Ser Pro Ser
1               5
```